US005834386A

United States Patent [19]
Cohen

[11] Patent Number: 5,834,386
[45] Date of Patent: Nov. 10, 1998

[54] NONWOVEN BARRIER

[75] Inventor: Bernard Cohen, Duluth, Ga.

[73] Assignee: Kimberly-Clark Worldwide, Inc., Neenah, Wis.

[21] Appl. No.: 690,587

[22] Filed: Jul. 31, 1996

Related U.S. Application Data

[63] Continuation-in-part of Ser. No. 504,209, Jul. 19, 1995, abandoned, and a continuation-in-part of Ser. No. 648,451, May 15, 1996, which is a continuation of Ser. No. 266,293, Jun. 27, 1994, abandoned.

[51] Int. Cl.⁶ ...................................................... B32B 5/06
[52] U.S. Cl. .................................. 442/382; 55/DIG. 39; 128/205.27; 128/206.21; 156/62.2; 156/62.4; 428/903; 442/340; 442/400; 442/401; 442/414
[58] Field of Search ..................................... 442/382, 340, 442/414, 400, 401; 428/903; 128/205.27, 206.21; 156/62.2, 62.4; 55/DIG. 39

[56] References Cited

U.S. PATENT DOCUMENTS

| | | | |
|---|---|---|---|
| 3,855,046 | 12/1974 | Hansen et al. | 161/150 |
| 4,103,062 | 7/1978 | Aberson et al. | 428/283 |
| 4,620,785 | 4/1997 | Watt et al. | 428/219 |
| 4,714,647 | 12/1987 | Shipp, Jr. et al. | 428/212 |
| 5,257,982 | 11/1993 | Cohen et al. | 604/378 |
| 5,308,674 | 5/1994 | Zafiroglu | 428/102 |
| 5,436,066 | 12/1993 | Chen | 428/288 |
| 5,455,108 | 10/1995 | Quincy et al. | 428/266 |
| 5,491,022 | 2/1996 | Smith | 428/224 |
| 5,552,012 | 9/1996 | Morris et al. | 156/272.4 |
| 5,637,165 | 6/1997 | Chen | 156/62.2 |

FOREIGN PATENT DOCUMENTS

| | | |
|---|---|---|
| 0 478 011 | 4/1992 | European Pat. Off. . |
| 0 520 798 | 12/1992 | European Pat. Off. . |
| 0575629 | 7/1993 | European Pat. Off. . |
| 0 754 796 | 1/1997 | European Pat. Off. . |
| 44 47 152 | 7/1995 | Guadeloupe . |
| 2 026 379 | 2/1980 | United Kingdom ............ D06M 9/00 |
| 2 242 142 | 9/1991 | United Kingdom ............ B03C 3/28 |
| 90/11784 | 10/1990 | WIPO . |
| 92/16681 | 10/1992 | WIPO . |
| 93/09156 | 5/1993 | WIPO ............................. C08G 8/18 |
| WO 94/00166 | 1/1994 | WIPO . |
| 95/22646 | 8/1995 | WIPO . |
| 96/00093 | 1/1996 | WIPO . |
| 96/28597 | 9/1996 | WIPO . |
| 97/04155 | 2/1997 | WIPO . |

OTHER PUBLICATIONS

Copy of PCT Search Report for PCT/US97/10716 dated Nov. 28, 1997.
Database WPI, Section Ch, Week 8428, Derwent Publications Ltd., London, GB; Class A87, AN 84–173431, XP002008760, & JP,A,59 094 621 (Unitika KK), 31 May 1984, see abstract.
Patent Abstracts of Japan, vol. 10, No. 71 (C–334), 20 Mar. 1986 & JP,A,60 209220 (Kouken K.K.), 21 Oct. 1985, see abstract.
Patent Abstracts of Japan, vol. 6, No. 191 (C–127), 30 Sep. 1982 & JP,A,57 105217 (Nitta K.K.), 30 Jun. 1982, see abstract & Chemical Abstracts, vol. 97, No. 26, 27 Dec. 1982, Columbus, Ohio, US; abstract no. 2189001, "Fibrous Filtering Material", see abstract.
Patent Abstracts of Japan, vol. 11, No. 315 (C–451), 14 Oct. 1987 & JP,A,62 102809 (Mitsui Petrochem. Ind. Ltd.), 13 May 1987, see abstract & Database WPI, Section Ch, Week 8725, Derwent Publications Ltd., London, GB; Class A12, AN 87–172842 & JP,A,62 102 809 (Mitsui Petrochem. Ind. Co. Ltd.), 13 May 1987, see abstract.
Journal of Electrostatics, vol. 21, 1988, Amsterdam NL, pp. 81–98, XP002012022, P. A. Smith & G. C. East: "Generation of Triboelectric Charge in Textile Fibre Mistures, and their use as Air Filters", see document.

*Primary Examiner*—James J. Bell
*Attorney, Agent, or Firm*—Nancy M. Klembus; Joseph P. Harps; Jones & Askew

[57] ABSTRACT

A sterilizable nonwoven material which is subjected to electreting, and more particularly electrostatic electreting is provided. The nonwoven materials may include laminate nonwovens wherein one or more layers are subjected to electreting. The nonwoven material(s) may also be treated with an antistatic material before or after subjecting the same to electreting.

37 Claims, No Drawings

NONWOVEN BARRIER

CROSS REFERENCE TO RELATED APPLICATIONS

This application is a continuation-in-part of application Ser. No. 08/504,209, filed Jul. 19, 1995, now abandoned and a continuation-in-part of pending application Ser. No. 08/648,451, filed May 15, 1996 pending, which is a continuation of application Ser. No. 08.266,293, filed Jun. 27, 1994, now abandoned.

FIELD OF THE INVENTION

The present invention is directed to bacterial barrier fabrics. More particularly, the present invention is directed to nonwoven microbial barrier fabrics for use as sterilization wrap, surgical draping, surgical gowns, cover garments, such as over-suits, and the like.

BACKGROUND OF THE INVENTION

As is generally known, surgical gowns, surgical drapes, surgical face masks and sterile wrap (hereinafter collectively "surgical articles") have been designed to greatly reduce, if not prevent, the transmission through the surgical article of liquids and/or airborne contaminates. In surgical procedure environments, such liquids sources include the gown wearer's perspiration, patient liquids, such as blood and life support liquids such as plasma and saline. Examples of airborne contaminates include, but are not limited to, biological contaminates, such as bacteria, viruses and fungal spores. Such contaminates may also include particulate material such as, but not limited to, lint, mineral fines, dust, skin squames and respiratory droplets. A measure of a fabrics ability to prevent the passage of such airborne materials is sometimes expressed in terms of "filtration efficiency".

Many of these surgical articles were originally made of cotton or linen and were sterilized prior to their use in the operating room. Such surgical articles fashioned from these materials, however, permitted transmission or "strike-through" of various liquids encountered in surgical procedures. In these instances, a path was established for transmission of biological contaminates, either present in the liquid or subsequently contacting the liquid, through the surgical article. Additionally, in many instances surgical articles fashioned from cotton or linen provided insufficient barrier protection from the transmission therethrough of airborne contaminates. Furthermore, these articles were costly, and of course laundering and sterilization procedures were required before reuse.

Disposable surgical articles have largely replaced linen surgical articles. Advances in such disposable surgical articles include the formation of such articles from totally liquid repellent fabrics which prevent strike-through. In this way, biological contaminates carried by liquids are prevented from passing through such fabrics. However, in some instances, surgical articles formed from nonporous films, while being liquid and airborne contaminate impervious, are, or become over a period of time, uncomfortable to wear.

In some instances, surgical articles fashioned from liquid repellent fabrics, such as fabrics formed from nonwoven polymers, sufficiently repel liquids and are more breathable and thus more comfortable to the wearer than nonporous materials. However, the improvements in comfort and breathability provided by such nonwoven fabrics have generally occurred at the expense of barrier properties or filtration efficiency.

While the focus thus far has been directed to surgical articles, there are many other garment or over-garment applications, such as personal protective equipment applications, whose designers require both fabric comfort and filtration efficiency. Other personal protective equipment applications include, but are not limited to, laboratory applications, clean room applications, such as semiconductor manufacture, agriculture applications, mining applications, and environmental applications.

Therefore, there is a need for garment materials and methods for making the same which provide improved breathability and comfort as well as improved filtration efficiency. Such improved materials and methods are provided by the present invention and will become more apparent upon further review of the following specification and claims.

SUMMARY OF THE INVENTION

In response to the above problems encountered by those of skill in the art, the present invention provides a steam sterilizable nonwoven material, such as nonwoven fabrics, formed from polymer fibers. The nonwoven materials of the present invention are formed by subjecting at least a portion of the nonwoven material to electreting and then sterilizing the nonwoven material. The nonwoven material may be, subjected to electreting followed by sterilization or sterilization followed by electreting. The sterilization procedure may be any method of sterilizing a solid material including, but not limited to, steam sterilization, ethylene oxide sterilization, plasma sterilization or ozone sterilization. The nonwoven material may also be treated with an antistatic material before or after subjecting the nonwoven material to electreting.

These methods further include positioning another nonwoven material in a juxtaposed relationship with the first nonwoven material. Portions of the other, or second, nonwoven material may be subjected to electreting before or after sterilization. The second nonwoven material may also be treated with an antistatic material before or after being subjected to electreting.

The nonwoven materials includes a sterilized web formed from fibers of a polymer wherein a portion of these fibers have been subjected to electreting. The sterilized nonwoven composition may also include an antistatic material present about portions thereof. The above nonwoven composition may further include a second web in a juxtaposed relationship to the first web. The second web may be formed from polymer fibers wherein a portion of these fibers may be subjected to electreting. An antistatic treatment may also be present about portions of the second web.

The composition of the present invention further includes a nonwoven material including a first web formed from fibers of a polymer, wherein at least a portion of these fibers have been subject to electreting and wherein an antistatic material is present about portions of the first web. This composition may further include a second web formed from fibers of a polymer, wherein the polymer is positioned in a juxtaposed relationship with the first web. The second web may also be subjected to electreting.

These and other features and advantages of the present invention will become apparent after a review of the following detailed description of the disclosed embodiments and the appended claims.

DETAILED DESCRIPTION

Disclosed herein are compositions, and methods of making the same, which improved both the airborne contaminate barrier and filtration efficiency of a web formed from polymer fibers. Among the applications for such compositions and methods are included, but not limited to, applications requiring sterilizable, breathable materials having high airborne contaminate barrier properties. Such materials have application in surgical articles, such as gowns, drapes, sterile wrap and face mask, as well as other non-surgical applications such as agriculture, mining, clean room and environmental applications.

As used herein, the term "dielectric" means a material, such as a polymer, which is an electrical insulator or in which an electric field can be sustained with a minimum dissipation of power. A solid material is a dielectric if its valence band is full and is separated from the conduction band by at least 3 eV. This definition is adopted from the McGraw-Hill Encyclopedia of Science & Technology, 7th Edition, Copyright 1992.

As used herein, the term "nonwoven fabric" refers to a fabric that has a structure of individual fibers or filaments which are interlaid, but not in an identifiable repeating manner.

As used herein the term "spunbonded fibers" refers to fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et al which are all herein incorporated by reference.

As used herein the term "meltblown fibers" means fibers formed by extruding a molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to form a fabric of randomly disbursed meltblown fibers. Meltblowing is described, for Example, in U.S. Pat. No. 3,849,241 to Buntin, U.S. Pat. No. 4,307,143 to Meitner et al., and U.S. Pat. No. 4,663,220 to Wisneski et al which are all herein incorporated by reference.

Polymers are well suited for the formation of nonwoven materials which are useful in the practice of the present invention. Nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of dielectric materials including, but not limited to, polyesters, polyolefins, nylon and copolymer of these materials. The fibers may be relatively short, staple length fibers, typically less than 3 inches, or longer more continuous fibers such as are produced by a spunbonding process.

It has been found that nonwovens formed from polyolefin-based fibers are particularly well-suited for the above applications. Examples of such nonwovens are the polypropylene nonwovens produced by the Assignee of record, Kimberly-Clark Worldwide, Inc. And more particularly, the spunbonded, meltblown, spunbonded material produced by Kimberly-Clark Worldwide, Inc.

This spunbonded, meltblown, spunbonded material may be made from three separate layers which are laminated to one another. Such a method of making this laminated material is described in commonly assigned U.S. Pat. No. 4,041,203 to Brock et al. which is incorporated herein in its entirety by reference. Alternatively, the spunbond, meltblown, spunbond material may be made by first forming a spunbonded, meltblown laminate. The spunbonded, meltblown laminate is formed by applying a layer of meltblown on to a layer of spunbonded. The second layer of spunbonded is then applied to the meltblown side of the previously formed spunbonded, meltblown laminate. Generally, the two outer layers provide the nonwoven fabric with strength while the inner layer provides barrier properties.

The nonwoven web of the present invention may be formed from a single layer or multiple layers. In the case of multiple layers, the layers are generally positions in a juxtaposed or surface-to-surface relationship and all or a portion of the layers may be bound to adjacent layers. The nonwoven web may also be formed from a plurality of separate nonwoven webs wherein the separate nonwoven webs may be formed from single or multiple layers. In those instances where the nonwoven web includes multiple layers, the entire thickness of the nonwoven web may be subjected to electreting or individual layers may be separately subjected to electreting and then combined with other layers in a juxtaposed relationship to form the finished nonwoven web.

The terms "electret" or "electreting" means a treatment that imparts charges to a dielectric material such as polyolefins. The charge includes layers of positive or negative charges trapped at or near the surface of of the polymer, or charge clouds stored in the bulk of the polymer. The charge also includes polarization charges which are frozen in alignment of the dipoles of the molecules. Methods of subjecting a material to electreting are well known by those skilled in the art. These methods include, for example, thermal, liquid-contact, electron beam and corona discharge methods. One particular technique of subjecting a material to electrostatic electreting is the technique disclosed in U.S. Pat. No. 5,401,466, and is herein incorporated in its entirety by reference. This technique involves subjecting a material to a pair of electrical fields wherein the electrical fields have opposite polarities.

Sterilization of the nonwoven web may be accomplished by several techniques including, but not limited to, ethylene oxide sterilization, steam sterilization, plasma sterilization, or ozone sterilization techniques. Ozone sterilization is described in U.S. Pat. No. 5,266,275; 5,344,622; 5,333,355; 5,280876; 5,145,350;. Plasma sterilization is described for example in U.S. Pat. Nos. 5,084,239. In those instances when the nonwoven web is used to wrap surgical instruments, steam sterilization techniques are commonly used although other sterilization techniques can be used. In such instances, the unsterile instruments are first wrapped in the nonwoven web. The wrapped instruments are then sterilized. The instruments, still wrapped, are then removed from the sterilizing equipment and are stored in the wrapping material until needed. When needed, the wrapping web is removed making the instruments available for handling.

For steam sterilization, the steam sterilization cycle may vary dependent upon type of sterilizer and the size/quantity of the items being sterilized. For example, the time and temperature parameters for gravity-displacement cycles may range from 10 to 15 minute exposure time at 270° F. to 275° F. to 15 to 30 minute exposure time at 250° F. to 254° F. For prevacuum cycles, the time and temperature parameters may be 3 to 4 minutes at 270° F. to 275° F. And for steam-flush pressure-pulse cycles, the time and temperature parameters may range from 3 to 4 minutes at 270° F. to 275° F. to 20 minutes at 250° F. to 254° F.

Sterilization of the web may also be accomplished by ethylene oxide sterilization. In those instances when it is desired to sterilize surgical instruments by ethylene oxide, the surgical instruments may be wrapped in a nonwoven web. The entire package may then be subjected to an ethylene oxide sterilization cycle. When the ethylene oxide sterilization cycle is completed, the instruments, still wrapped, are then removed from the ethylene oxide sterilizing equipment and are stored in the wrapping material until needed. When needed, the wrapping web is removed making the instruments available for handling.

When ethylene oxide is used to sterilize, ethylene oxide sterilization cycle may vary dependent upon type of sterilizer and the size/quantity of the items being sterilized. In the examples described below, ethylene oxide sterilization was accomplished by using either a RSSA Chamber J88-39 or J88-59, made by Vacu Dyne, IL. Generally, the ethylene oxide sterilization cycle includes a preconditioning phase, a sterilization phase and a de-gassing phase. The process parameters for each of these phases are provided below.

A. Preconditioning

| Process Parameters | Set Point |
| --- | --- |
| Temperature | 115° F. |
| Relative Humidity | 63% |
| Holding time | 18 hours |

B. Sterilization

| Process Parameters | Set Point |
| --- | --- |
| Chamber Temperature during exposure | 130.0 F. |
| Chamber Temperature at all other times | 130.0 F. |
| Initial Evacuation | 1.2" Absolute |
| Leak Test | 1.2" Absolute |
| Leak Test Dwell | 5 minutes |
| Nitrogen Dilution | 3.2" Absolute |
| Evacuation | 1.2" Absolute |
| Humidity Injection Pressure Increase to | 2.9" Absolute |
| Humidification Dwell Time | 30 minutes |
| ETC Injection Pressure | 15" Absolute |
| Time to inject gas | NA |
| Cycle Exposure | 2 hours |
| Exposure Pressure | 15" Absolute |
| Exposure Temperature | 130.0 F. |
| 1st Re-evacuation | 6.0" Absolute |
| 1st Nitrogen Inbleed | 50.0" Absolute |
| 2nd Re-evacuation | 1.6" Absolute |
| 2nd Nitrogen Inbleed | 50.0" Absolute |
| 3rd Re-evacuation | 1.6" Absolute |

C. Degassing Parameters

| Process Parameters | Set Point |
| --- | --- |
| Degassing Time | 24.0 hours |
| Degassing Temperature | 130° F. |

Plasma sterilization of the nonwoven fabric may be accomplished by subjecting the nonwoven fabric to hydrogen peroxide or peracetic acid plasma at a sufficient pressure for a sufficient time. In those instances when the nonwoven fabric is used to wrap surgical instruments or other unsterile supplies, such items are placed in an instrument tray. The instrument tray is then generally wrapped with two juxtaposed sheets of material commonly referred to as sterilization wrap. Sterilization wrap is usually a woven or nonwoven material which, when wrapped around the tray or package contents in a certain prescribed manner, will permit the entry of sterilizing vapor/gas or other medium to sterilize the contents of the tray while denying the ingress of contaminants such as bacteria and other infection causing materials after sterilization. Once sterilization is complete, the instruments and other supplies, still wrapped, are then removed from the plasma sterilizing equipment and are stored in the wrapping material until needed. When needed, the wrapping material is removed making the instruments available for handling. The plasma sterilization cycle may vary dependent upon the type of sterilizer, the size/quantity of the items being sterilized and the composition of the chemical precursor of the active species of the plasma.

In those instances where the web is used in or around flammable materials or static charge build-up and/or discharge is a concern, the web may be treated with any number of antistatic materials. In these instances, the antistatic material may be applied to the web by any number of well known techniques including, but not limited to dipping the web into a solution containing the antistatic material or by spraying the web with a solution containing the antistatic material. In some instances the antistatic material may be applied to both the external surfaces of the web and the bulk of the web. In other instances, the antistatic material may be applied to portions of the web, such as a selected surface or surfaces thereof.

Of particular usefulness is the antistatic material known as ZELEC®, an alcohol phosphate salt product of the DuPont Corporation. The nonwoven web may be treated with the antistatic material either before or after subjecting the web to electreting. Furthermore, some or all of the material layers may be treated with the antistatic material. In those instances where only some of the material layers are treated with antistatic material, the non-treated layer or layers may be subjected to electreting prior to or after combining with the antistatic treated layer or layers.

In the electreted webs according to the present invention, bacterial filtration efficiencies are greater than approximately 90% with a desirable bacterial filtration efficiency of greater than approximately 92% with a most desirable bacterial filtration efficiency of greater than approximately 94%.

Maximum bacterial efficiency is 100%. Bacterial filtration efficiency analysis is measured by Nelson Laboratories of Salt Lake City, Utah. The procedure used to determine these BFEs is described in. Nelson Laboratories Protocol No. ARO/007B in accordance with MIL Spec 36954C, 4.4.1.1.1 and 4.4.1.2.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Kimberly-Clark manufactures a series of single sheet laminate nonwoven web materials made from spunbonded-meltblown-spunbonded (SMS) layers. These materials are available in a variety of basis weights. The nonwoven web materials used in the Examples were such single sheet laminate materials sold by Kimberly-Clark under the trademark KIMGUARD® Heavy Duty Sterile Wrap. The basis weight of this material is 2.2 oz/sq yd. Both spunbonded layers have a basis weight of 0.85 oz/sq yd and the meltblown layer has a basis weight of 0.50 oz/sq yd.

The method used to subject the samples reported in Tables 1–4 to electrostatic electreting is described in the above referenced U.S. Pat. No. 5,401,466.

Referring now to Table 1, a summary of bacterial filtration efficiency (BFE) test results and standard deviation (SD) are reported for three categories investigated for Heavy Duty KIMGUARD® Sterile Wrap. The first category, "Unelectreted" reports the average BFE for eleven samples of ZELEC® treated and eleven samples of nonZELEC® treated KIMGUARD® material. These samples were not subjected to electreting or steam sterilization.

The second category, "Electreted", reports the average BFE for eleven samples of ZELEC® treated and eleven samples of non-ZELEC® treated KIMGUARD® material which were subject to electreting but not steam sterilization.

The third category, "Electreted/Sterilized" reports the average BFE for eleven samples of ZELEC® treated and eleven samples of non-ZELEC® treated KIMGUARD® material which were first electreted then steam sterilized. Sterilization of these samples was accomplished in an Amsco 2021 Gravity Sterilizer, a product of American Sterilizer Co. of Erie, Pa. Samples were sealed in a Baxter DUAL PEEL™ Self Seal Pouch. The sealed pouches were exposed to 250° F. at 15 psi steam for 20 minutes with a dry time of 5 minutes. After sterilizing, the above samples were analyzed by Nelson Laboratories for Bacterial Filtration Efficiency testing.

TABLE 1

Bacterial Filtration Efficiency
(KIMGUARD ® Heavy Duty Sterile Wrap)

| Description | Unelectreted | Electreted | Electreted/Sterilized |
|---|---|---|---|
| ZELEC ® | 85.55 +/− 2.38 | 93.85 +/− 3.67 | 95.87 +/− 0.99 |
| Non-ZELEC ® | 82.18 +/− 1.66 | 96.36 +/− 1.72 | 93.64 +/− 2.72 |

As previously stated, Nelson Laboratories of Salt Lake City, Utah preformed the above BFE analysis. The procedure used to determine these BFEs is described in Nelson Laboratories Protocol No. ARO/007B in accordance with MIL Spec 36954C, 4.4.1.1.1 and 4.4.1.2.

EXAMPLE 2

Further analysis of the Heavy Duty KIMGUARD Sterile Wrap (2.2 oz) were conducted to determine BFE and the charge on the samples for both pre- and poststeam sterilizing. Steam sterilization of the samples reported in Example 2 was accomplished using the steam sterilization procedure reported in Example 1. The BFE results reported in Table 2 were the product of Nelson Laboratories using the protocol described in Example 1. These BFE results represent the average of eleven non-antistatic treated samples.

TABLE 2

Bacterial Filtration Efficiency
(KIMGUARD ® Heavy Duty Sterile Wrap)

| Description | BFE | SD % | Electret Pre | Electret Post |
|---|---|---|---|---|
| Unelectreted | 90.6 | 2.3 | | |
| Electreted | 98.8 | 0.31 | 800–1000 v/cm$^2$ | |
| Electreted\Sterilized | 94.4 | 2.0 | | 100–180 v/cm$^2$ |

After electreting but before steam sterilizing, a voltage of between 800 to 1,000 volts/cm, positive on one side of the material and negative on the other side of the material, was recorded. After steam sterilizing, a voltage of between 100 to 180 volts/sq cm, positive on one side and negative on the other side, was recorded. In both instances, voltage was measured using an Electrostatic Voltmeter (Trek Model 344, Trek, Inc. Median, N.Y.) by taking ten readings on each side of the samples.

EXAMPLE 3

Further barrier properties for SMS fabric samples were investigated, Table 3 reports the barrier property results for KIMGUARD® Heavy-Duty Sterile Wrap (KIM) and SPUNGUARD® Regular Sterilization Wrap (SPU). SPUNGUARD® Regular Sterilization Wrap is also a spunbondED, meltblown, spunbondED material having a basis weight of 1.05 oz/sq yd (0.35/0.35/0.35). These categories included ZELEC® treated and non-ZELEC® treated materials, electreted and non-electreted, sterilized and non-sterilized material.

The electreted and sterilized samples were prepared according to the electreting and sterilizing procedures described in Example 1 except that all sterilized sample pouches were conditioned at laboratory ambient environment for at least 4 hours prior to testing. For samples 1 and 2, the barrier properties were measured using the Nelson procedures described in Example 1. For samples 3–13, the barrier properties were measured using a microbial challenge procedure described below.

In runs 3–13, a six port exposure chamber was used. Five of the ports accommodated five separate samples. The challenge control filter material was positioned in the sixth port. Three conditions were maintained in the microbial challenge test. These were: first, a 2.8 LPM (Liters Per Minute) flowrate through each of the ports; second, an exposure time of fifteen minutes followed by a chamber exhaust of fifteen minutes, and; third, a microbial challenge that results in $1 \times 10^6$ CFU's (Colony Forming Units) per port. *Bacillus subtilis ss globigii* spores, purchased from Amsco (Part No. NA-026, P-764271-022) was used to make the working spore suspension of $1 \times 10^6$ CFUs per port recovery.

TABLE 3

| Sample | Product | ZELEC ® | Electreted | Sterilized | Avg % Red | SD | n |
|---|---|---|---|---|---|---|---|
| 1 | SPU | No | No | Yes | 71.5 | 9.1 | 25 |
| 2 | SPU | No | Yes | Yes | 87.2 | 3.1 | 25 |
| 3 | KIM | Yes | No | Yes | 69.4 | 5.7 | 15 |
| 4 | KIM | Yes | Yes | Yes | 80.8 | 9.1 | 15 |
| 5 | KIM | Yes | Yes | No | 97.2 | 1.1 | 15 |
| 6 | KIM | Yes | No | Yes | 80.1 | 9.2 | 15 |
| 7 | KIM | Yes | Yes | Yes | 88.9 | 5.7 | 15 |
| 8 | KIM | Yes | Yes | No | 94.6 | 2.7 | 15 |
| 9 | KIM | Yes | No | Yes | 73.9 | 7.6 | 15 |
| 10 | KIM | Yes | Yes | Yes | 86.2 | 4.1 | 15 |
| 11 | KIM | No | No | Yes | 66.8 | 11.9 | 15 |
| 12 | KIM | No | Yes | Yes | 94.5 | 2.8 | 5 |
| 13 | KIM | No | Yes | No | 98.2 | 0.7 | 15 | n—Number of fabric samples.

The average percent reduction (Avg%Red) is a measurement of filtration efficiency. The Avg%Red is an expression of the reduction of number of colony forming units (CFUs) or bacteria passing through a sample compared to the number CFUs in the challenge control filter material. The Avg%Red was calculated by subtracting the number of CFUs passing through a sample from the number of CFUs passing through the challenge control filter material and dividing this number by the number of CFUs for the challenge filter material. The result was then multiplied by 100 to convert to percent.

Table 3 demonstrates that filtration properties of the steam sterilized nonwoven samples are improved by the electreting the fabric samples (Samples 2, 4, 7, 10, and 12) as compared to samples which have not been subjected to electreting (Samples 1, 3, 6, 9, and 11).

EXAMPLE 4

Table 4 reports charge data for the top and bottom surfaces of 2.2 oz. KIMGUARD® fabric samples subjected to various conditions. As noted in Table 4, one of the KIMGUARD® samples was treated with ZELEC® and the other was not. Except as otherwise indicated, the measurements were made on separate samples. Each sample had a general dimension of about 10"×10". The area of each sample measured had a general dimension of about 6"×6". Measurements were taken each ½" in a 12×12 matrix. The charge number reported is an averaged number. The equipment used to measure charge was the same as described in Example 2.

EXAMPLE 5

Kimberly-Clark manufactures a series of single sheet laminate nonwoven web materials made from three layers of fibrous material, i.e., spunbonded-meltblown-spunbonded (SMS) layers. These materials are available in a variety of basis weights. The two nonwoven webs used in these Examples were such single sheet laminate materials sold by Kimberly-Clark. Each of the nonwoven webs had a basis weight of 2.2 osy (ounces per square yard). Both spunbonded layers had a basis weight of 0.85 osy and the meltblown layer had a basis weight of 0.50 osy. One of the nonwoven webs was a ZELEC® treated laminate and is sold by Kimberly-Clark the under the mark KIMGUARD® Heavy Duty Sterile Wrap and is designated in Table 5 as "KIMGUARD®".

The other nonwoven web, designated in Table 5 as "RSR" also had a basis weight of 2.2 osy but was not treated with an antistatic material. RSR fabric is the same as KIMGUARD® fabric except it is not treated with the antistatic agent ZELEC®. Both spunbond layers had a basis weight of 0.85 osy and the meltblown layer had a basis weight of 0.50 osy. The method used to subject these webs to electret treating is described in the above referenced U.S. Pat. No. 5,401,466.

TABLE 5

| | | | | After EO Treatment | | |
|---|---|---|---|---|---|---|
| Material | Side | Received | Electreted | Sample 1 | Sample 2 | Sample 3 |
| KIMGUARD ® (ZELEC ®) | A | -2.8 | -125 | -4.2 | 27.2 | — |
|  | B | +1.6 | -15 | 24.1 | -5.4 | — |
| RSR (Non-ZELEC ®) | A | -61 | +272 | -89 | -130 | -138 |
|  | B | -87 | -432 | -90 | -46 | +54 |

The surface charge for both KIMGUARD® and RSR fabrics were analyzed and the data reported in Table 5. The charge data for each side of these fabrics was recorded for both before ("AS RECEIVED") and after electreting ("ELECTRETED"). Charge data were also recorded for ethylene oxide sterilized fabric samples which were first electreted and then ethylene oxide sterilized ("AFTER EO TREATMENT"). As noted in this example, the KIMGUARD® samples were treated with ZELEC® and the RSR samples were not. Charge measurements were taken at 36

TABLE 4

AVERAGE SURFACE VOLTAGE OF SAMPLES OF 2.2 OZ KIMGUARD ® STERILE WRAP

| | | Sample # | | | | | |
|---|---|---|---|---|---|---|---|
| Material | Side | 1 As Received | 2 Charge | 3 Sterilizer 20 min. in Duel Peel Pouch | 4 Sterilizer 60 min. in Duel Peel Pouch | 5 Sample #3 No Pouch Sterilizer 20 min. | 6 Sample #3 No Pouch Sterilizer 60 min. |
| KIMGUARD ® ZELEC ® | A B | -2.8 1.6 | -125 -15 | -51 -48 | -100 -169 | 30 72 | -43 66 |
| KIMGUARD ® Non-ZELEC ® | A B | -61 -87 | 272 -432 | 239 -265 | -353 -243 | -146 -232 | -354 -223 |

Notes:
Sample #5 rerun of #3 without pouch
Sample #6 rerun of #4 without pouch separate surface locations on each sample. For the categories, i.e., "AS RECEIVED" and "ELECTRETED", the KIMGUARD® and RSR samples were each single large sheets of material. Each such sheets were then portioned into eleven smaller samples. Sterilization and filtration data reported in Example 6 were derived from these smaller samples.

Charge measurements reported are averaged values of positive (+) or negative (−) volts per cm$^2$. The equipment used to measure charge was an Electrostatic Voltmeter (Trek Model 344, Trek, Inc. Median, N.Y.).

As illustrated by the above data, the ethylene oxide sterilization process generally diminished the overall surface charge for both the electret treated KIMGUARD® and the RSR material. It should be noted that the reduction of the overall surface charge does not effect the bacterial filtration efficiency of the treated fabric as illustrated in Example 6.

EXAMPLE 6

A summary of the average bacterial filtration efficiency (BFE) test results and standard deviation (SD) are reported for the two categories investigated for KIMGUARD® in Table 6. The first category, reported in Table 6 is the "Nelson BFE". "Nelson BFE" stands for Nelson Laboratory's (Salt Lake City, Utah.) bacterial filtration efficiency test. The procedure used to determine these BFEs is described in Nelson Laboratories' Protocol No. AR0/007B in accordance with MIL Spec 36954C, 4.4.1.1.1 and 4.4.1.2. This category includes the average BFE for 11 KIMGUARD® fabric samples which were electret-treated then ethylene oxide-sterilized ("KIMGUARD®@/Electret/EO") and 11 non-electret-treated KIMGUARD® fabric samples which were ethylene oxidesterilized ("KIMGUARD®@/E0").

The second category reported in Table 6 is "Microbial Challenge BFE". This category includes the average BFEs for the KIMGUARD® samples.

The Microbial Challenge BFE procedure utilized a six port exposure chamber. Five of the ports accommodated five separate samples. The challenge control filter material was positioned in the sixth port. Three conditions were maintained in the microbial challenge test. These were: first, a 2.8 LPM (Liters Per Minute) flow rate through each of the ports; second, an exposure time of fifteen minutes followed by a chamber exhaust of fifteen minutes, and; third, a microbial challenge that results in 1×10$^6$ CFU's (Colony Forming Units) per port. Bacillus subtilis ss globigii spores, purchased from Amsco (Part No. NA-026, P764271-022) were used to make the working spore suspension of 1×10$^6$ CFUs per port recovery.

The value reported is an expression of the reduction of number of colony forming units (CFUs) or bacteria passing through a sample compared to the number of CFUs passing through the challenge control filter material. This value was derived by subtracting the number of CFUs passing through a sample from the number of CFUs passing through the challenge control filter material. The difference in the number of CFUs passing through these materials is then divided by the number of CFUs passing through the challenge filter material and then multiplied by 100 to convert to percent.

TABLE 6

| Sample | Nelson BFE | Microbial Challenge BFE |
|---|---|---|
| KIMGUARD@/Electret/EO | 97.51 +/− 0.39 | 96.44 +/− 4.51 |
| KIMGUARD@/EO | 89.96 +/− 1.04 | 79.04 +/− 6.50 |

Example 7 summarizes the average Nelson BFE and the Microbial Challenge BFE categories for the RSR nonwoven materials. The procedures for both the Nelson BFE and Microbial Challenge BFE for the RSR materials were identical to the Nelson BFE and Microbial Challenge BFE procedures describe above. "RSR/Electret/EO" stands for RSR electret-treated then ethylene oxide-treated samples. "RSR/Electret" stands for RSR electret-treated samples. "RSR/EO" stands for RSR ethylene oxide-sterilized samples. Eleven samples of each class of RSR material described above were analyzed and the results averaged.

TABLE 7

| Sample | Nelson BFE | Microbial Challenge BFE |
|---|---|---|
| RSR/Electret/EO | 96.92 +/− 0.91 | 97.56 +/− 0.83 |
| RSR/Electret | 95.75 +/− 0.60 | 98.91 +/− 0.64 |
| RSR/EO | 79.73 +/− 3.20 | 79.82 +/− 5.96 |

Example 7 demonstrates that barrier properties of an ethylene oxide sterilizable material are improved when such material is first subjected to electreting, in particular electrostatic electreting, and then ethylene oxide sterilized as compared to the same material which is not subjected to electreting prior to ethylene oxide sterilization. It will be further observed that the decrease in the surface charge which occurred after ethylene oxide sterilization (Table 5) did not significantly affect the barrier properties of these materials.

EXAMPLE 7

Sample 1 consisted of six sheets of the above described 2.2 osy KIMGUARD® Heavy Duty Sterile Wrap containing about 0.03 percent by weight of ZELEC®, the antistatic treatment previously described, which was topically applied. The dimension of each sheet was 27"×34".

Sample 2 consisted of two sheets of the above described 2.2 osy KIMGUARD® Heavy Duty Sterile Wrap but without any ZELEC®. Both Sample 1 and 2 were subjected to electrostatic electreting as described above.

Three, 10"×10"×3½" plastic surgical trays were each wrapped with two sheets of Sample 1 material. One, 10"× 10"×3 ½" plastic surgical tray was wrapped with the two sheets of Sample 2 material. The sheet contacting the instrument tray is referred to as the "Bottom Layer" and the sheet overlying the Bottom layer is referred to as the "Top Layer".

The four double wrapped surgical trays were sterilized in a STERRAD™ plasma sterilizer model no. 100 (Advanced Strerilization Products Johnson & Johnson Medical Inc.). After plasma sterilization, the bacterial filtration efficiencies for the plasma sterilized Top and Bottom Layers of Sample 1 and 2 were analyzed by Nelson Laboratories. Table 8 reports the data for the plasma sterilized Sample 1, Top and Bottom Layers and Table 9 reports the data for the plasma sterilized Sample 2, Top and Bottom Layers. The data reported in Tables 8 and 9 are the average of eleven measurements taken from different locations on each layer of material.

TABLE 8

2.2 osy KIMGUARD ® BFE % Electreted With ZELEC ®

| Top Layer | Bottom Layer |
|---|---|
| 95.2 +/− 0.93 | 97.8 +/− 0.53 |
| 94.8 +/− 0.76 | 98.7 +/− 0.41 |
| 95.6 +/− 0.84 | 98.7 +/− 0.22 |

TABLE 9

2.2 osy KIMGUARD ® BFE % Electreted Without ZELEC ®

| Top Layer | Bottom Layer |
|---|---|
| 94.3 +/− 1.98 | 98.2 +/− 0.66 |

EXAMPLE 8

Sample 3 consisted of six sheets of the above described 2.2 osy KIMGUARD® Heavy Duty Sterile Wrap containing about 0.03 percent by weight of ZELEC®, the antistatic treatment previously described, which was topically applied. The dimension of each sheet was 27"×36".

Sample 4 consisted of two sheet of the above described 2.2 osy KIMGUARD® Heavy Duty Sterile Wrap but without any ZELEC®. Samples 3 and 4 were not subjected to electrostatic electreting.

Three, 10 inch by 10 inch by 3 ½ inch plastic surgical trays were each wrapped with two sheets of Sample 3 material. One, 10 inch×10 inch×3 ½ inch plastic surgical tray was wrapped with the two sheets of Sample 4 material. The sheet contacting the instrument tray is referred to as the "Bottom Layer" and the sheet overlying the Bottom layer is referred to as the "Top Layer".

The four double wrapped surgical trays were sterilized in the STERRAD™ plasma sterilizer. After plasma sterilization, the bacterial filtration efficiencies for the plasma sterilized Top and Bottom Sample Layers were analyzed by Nelson Laboratories. Table 10 reports the data for the plasma sterilized Sample 3, Top and Bottom Layers and Table 11 reports the data for the plasma sterilized Sample 4, Top and Bottom Layers. The data reported in Tables 10 and 11 are the average of eleven measurements taken from different locations on each layer of material.

TABLE 10

2.2 osy KIMGUARD ® BFE % With ZELEC ®

| Top Layer | Bottom Layer |
|---|---|
| 90.7 +/− 1.42 | 93.1 +/− 1.48 |
| 91.5 +/− 1.56 | 92.0 +/− 1.53 |
| 92.4 +/− 1.56 | 92.5 +/− 0.67 |

TABLE 11

2.2 osy KIMGUARD ® BFE % Without ZELEC ®

| Top Layer | Bottom Layer |
|---|---|
| 88.0 +/− 2.92 | 89.6 +/− 1.75 |

As demonstrated by the above Examples, the barrier properties of plasma sterilized non-woven materials are improved when these materials are subjected to electreting. It will be further observed that the barrier properties of a plasma sterilized antistatic treated non-woven materials are improved when these materials are subjected to electreting, for example electrostatic electreting.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

I claim:

1. A sterilized, electreted web having a Nelson bacterial filtration efficiency of at least 90%.

2. The web of claim 1, wherein the Nelson bacterial filtration efficiency is at least approximately 92%.

3. A sterilized, electreted web having a Nelson bacterial filtration efficiency of at least approximately 94%.

4. The web of claim 1, wherein the electreted web is a nonwoven web.

5. A sterilized, electreted nonwoven web having a Nelson bacterial filtration efficiency of at least 90%, wherein the nonwoven web comprises two outer layers separated by an intermediate layer wherein the two outer layers are spunbonded nonwoven layers and the intermediate layer is a meltblown layer.

6. The web of claim 1, further comprising an antistatic material.

7. The web of claim 1, wherein the web is sterilized by steam, ozone, plasma, or ethylene oxide.

8. A sterilized nonwoven web laminate comprising:

two outer layers separated by an intermediate layer, wherein the two outer layers are spunbonded nonwoven layers and the intermediate layer is a meltblown layer; and at least one of the layers is electreted.

9. The nonwoven web of claim 8, wherein all three layers are electreted.

10. The nonwoven web of claim 8, wherein at least one of the layers is treated with an antistatic material.

11. The nonwoven web of claim 8, wherein the web is sterilized by steam, ozone, plasma, or ethylene oxide.

12. The nonwoven web of claim 8, wherein the web has a Nelson bacterial filtration efficiency of at least 90%.

13. The nonwoven web of claim 8, wherein the Nelson bacterial filtration efficiency is at least approximately 92%.

14. The nonwoven web of claim 8, wherein the Nelson bacterial filtration efficiency is at least approximately 94%.

15. The web of claim 1, said web being free of an antibacterial additive.

16. The web of claim 1, said web being free of a charge-sustaining additive.

17. The web of claim 16, said web being free of an antibacterial additive.

18. The web of claim 3, further comprising an antistatic material.

19. The web of claim 18, wherein the antistatic material is an alcohol phosphate salt.

20. The web of claim 3, wherein the web is sterilized by steam, ozone, plasma, or ethylene oxide.

21. An article wrapped in a sterilized, electreted web, the web having a Nelson bacterial filtration efficiency of at least 90%.

22. An article wrapped in a sterilized, nonwoven web laminate wherein the nonwoven web laminate comprises two outer layers separated by an intermediate layer, wherein the two outer layers are spunbonded nonwoven layers and the intermediate layer is a meltblown layer, and at least one of the layers is electreted.

23. The article of claim 22, wherein at least one layer of the nonwoven web is treated with an antistatic material.

24. The article of claim 22, wherein the nonwoven web laminate has a Nelson bacterial filtration efficiency of at least 90%.

25. A method of manufacturing a fabric having a Nelson bacterial filtration efficiency of at least 90%, said method comprising sterilizing an electreted fabric.

26. The method of claim 25, wherein the fabric is sterilized prior to being subjected to electreting.

27. A method of manufacturing a fabric having a Nelson bacterial filtration efficiency of at least 90%. said method comprising sterilizing an electreted fabric, wherein the fabric is subjected to electreting prior to being sterilized.

28. The method of claim 25, wherein the fabric is a nonwoven fabric.

29. The method of claim 28, wherein the nonwoven fabric comprises a first and a second nonwoven fabrics positioned in juxtaposed relationship.

30. The method of claim 29, wherein the first and second nonwoven fabrics are positioned in juxtaposed relationship after the electreting step.

31. The method of claim 29, wherein the first nonwoven fabric is subjected to electreting and the second nonwoven fabric is not subjected to electreting.

32. The method of claim 25, wherein the fabric is treated with an antistatic material.

33. The method of claim 29, wherein the first nonwoven fabric is treated with an antistatic material.

34. The method of claim 29, wherein the second nonwoven fabric is treated with an antistatic material.

35. The method of claim 25, wherein the fabric is sterilized by steam, ozone, plasma, or ethylene oxide.

36. The method of claim 25, wherein the fabric has a Nelson bacterial filtration efficiency of at least 92%.

37. The method of claim 25, wherein the fabric has a Nelson bacterial filtration efficiency of at least 94%.

* * * * *